(12) United States Patent
Ahn et al.

(10) Patent No.: US 8,889,647 B2
(45) Date of Patent: Nov. 18, 2014

(54) RECOMBINANT PROTEIN FOR SIRNA DELIVERY AND COMPOSITION COMPRISING THE SAME

(71) Applicant: Korea Institute of Science and Technology, Seoul (KR)

(72) Inventors: Hyung-Jun Ahn, Seoul (KR); Ick-Chan Kwon, Seoul (KR); Kui-Won Choi, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/742,901

(22) Filed: Jan. 16, 2013

(65) Prior Publication Data

US 2014/0045914 A1    Feb. 13, 2014

(30) Foreign Application Priority Data

Aug. 10, 2012 (KR) .................. 10-2012-0087882

(51) Int. Cl.
   *C07H 21/04* (2006.01)
   *C07K 14/00* (2006.01)

(52) U.S. Cl.
   USPC ............. 514/44; 435/6; 435/91.1; 435/91.31; 435/455; 530/300; 530/350; 536/23.1; 536/24.5

(58) Field of Classification Search
   USPC .............. 435/6.1, 6.11, 91.1, 91.31, 455, 6; 514/1, 2, 44; 536/23.1, 24.5; 530/300, 530/350
   See application file for complete search history.

(56) References Cited

U.S. PATENT DOCUMENTS

| | | | | |
|---|---|---|---|---|
| 8,361,510 B2 * | 1/2013 | Lyon et al. | ............ | 424/490 |
| 2009/0180958 A1 * | 7/2009 | Koivistoinen et al. | ......... | 424/9.1 |
| 2010/0160262 A1 * | 6/2010 | Ott et al. | ............ | 514/150 |
| 2010/0209933 A1 * | 8/2010 | McReynolds et al. | ............ | 435/6 |
| 2013/0150287 A1 * | 6/2013 | Ahn et al. | ............ | 514/3.7 |

OTHER PUBLICATIONS

Jin et al., "Protein mediated miRNA detection and siRNA enrichment using p19", BioTechniques, Vo. 48, No. 6, Jun. 2010, pp. xvii-xxiii.
Mitra et al., "Structure-Activity Relationship Analysis of Peptides Targeting the EphA2 Receptor", Biochemistry, 49 (31), Aug. 10, 2010, pp. 6687-6695 (renumbered pp. 1-20).

* cited by examiner

*Primary Examiner* — Jane Zara
(74) *Attorney, Agent, or Firm* — Staas & Halsey LLP

(57) ABSTRACT

Recombinant proteins for siRNA delivery and a composition including same. These recombinant proteins include a p19 RNA binding protein and a target oriented peptide and can secure the stability of siRNAs from external attacks such as various degradation enzymes, have selective binding affinity to cancer cells by virtue of target-oriented peptides having various cancer cells as their target, and silence target genes by effectively delivering the siRNAs to cells and biological tissues by the release of the siRNAs to the cytoplasms after the cell penetration thereof. Therefore, they are expected to be effectively employed as siRNA delivery vehicles for siRNA therapeutic agents, cell-based drug screening compositions and research.

7 Claims, 16 Drawing Sheets
(8 of 16 Drawing Sheet(s) Filed in Color)

FIG. 1

```
         10          20          30          40          50
MERAIQGNDT REQANGERWD GGSGGITSPF KLPDESPSWT EWRLYNDETN 60          70          80          90         100
SNQDNPLGFK ESWGFGKVVF KRYLRYDRTE ASLHRVLGSW TGDSVNYAAS 110         120         130         140         150
RFLGANQVGC TYSIRFRGVS VTISGGSRTL QHLCEMAIRS KQELLQLTPV 160         170         180         190
EVESNVSRGC PEGIETFKKE SEGSGGGDEA DYSAYPDSVP MMS
```

SEQ ID NO. 1         SEQ ID NO. 2         SEQ ID NO. 3

SEQUENCE LISTING

```
<160> NUMBER OF SEQ ID NOS: 12

<210> SEQ ID NO 1
<211> LENGTH: 172
<212> TYPE: PRT
<213> ORGANISM: Artificial Sequence
<220> FEATURE:
<223> OTHER INFORMATION: p19 protein of Carnation Italian ringspot virus
<300> PUBLICATION INFORMATION:
<308> DATABASE ACCESSION NUMBER: GenBank CAA59481.1

<400> SEQUENCE: 1

Met Glu Arg Ala Ile Gln Gly Asn Asp Thr Arg Glu Gln Ala Asn Gly
 1               5                  10                  15

Glu Arg Trp Asp Gly Gly Ser Gly Gly Ile Thr Ser Pro Phe Lys Leu
                20                  25                  30

Pro Asp Glu Ser Pro Ser Trp Thr Glu Trp Arg Leu Tyr Asn Asp Glu
            35                  40                  45

Thr Asn Ser Asn Gln Asp Asn Pro Leu Gly Phe Lys Glu Ser Trp Gly
        50                  55                  60

Phe Gly Lys Val Val Phe Lys Arg Tyr Leu Arg Tyr Asp Arg Thr Glu
 65                  70                  75                  80

Ala Ser Leu His Arg Val Leu Gly Ser Trp Thr Gly Asp Ser Val Asn
                85                  90                  95

Tyr Ala Ala Ser Arg Phe Leu Gly Ala Asn Gln Val Gly Cys Thr Tyr
            100                 105                 110

Ser Ile Arg Phe Arg Gly Val Ser Val Thr Ile Ser Gly Gly Ser Arg
        115                 120                 125

Thr Leu Gln His Leu Cys Glu Met Ala Ile Arg Ser Lys Gln Glu Leu
    130                 135                 140

Leu Gln Leu Thr Pro Val Glu Val Glu Ser Asn Val Ser Arg Gly Cys
145                 150                 155                 160

Pro Glu Gly Ile Glu Thr Phe Lys Lys Glu Ser Glu
                165                 170

<210> SEQ ID NO 2
<211> LENGTH: 9
<212> TYPE: PRT
<213> ORGANISM: Artificial Sequence
<220> FEATURE:
<223> OTHER INFORMATION: linker peptide

<400> SEQUENCE: 2

Gly Ser Gly Gly Gly Asp Glu Ala Asp
 1               5

<210> SEQ ID NO 3
<211> LENGTH: 12
<212> TYPE: PRT
<213> ORGANISM: Artificial Sequence
<220> FEATURE:
<223> OTHER INFORMATION: YSA peptide
```

<400> SEQUENCE: 3

Tyr Ser Ala Tyr Pro Asp Ser Val Pro Met Met Ser
 1               5                  10

<210> SEQ ID NO 4
<211> LENGTH: 19
<212> TYPE: RNA
<213> ORGANISM: Artificial Sequence
<220> FEATURE:
<223> OTHER INFORMATION: sense strand of siRNA

<400> SEQUENCE: 4
uguagaugga cuugaacuc                                              19

<210> SEQ ID NO 5
<211> LENGTH: 19
<212> TYPE: RNA
<213> ORGANISM: Artificial Sequence
<220> FEATURE:
<223> OTHER INFORMATION: antisense strand of siRNA

<400> SEQUENCE: 5
ugaaguugca cuugaaguc                                              19

<210> SEQ ID NO 6
<211> LENGTH: 579
<212> TYPE: DNA
<213> ORGANISM: Artificial Sequence
<220> FEATURE:
<223> OTHER INFORMATION: Recombinant protein for siRNA delivery

<400> SEQUENCE: 6
atggaacgag ctatacaagg aaacgacact agggaacaag ctaacggtga acgttgggat    60
ggaggatcag gaggtatcac ttctcccttc aaacttcctg acgaaagtcc gagttggact   120
gagtggcggc tatataacga tgagacgaat tcgaatcaag ataatcccct tggtttcaag   180
gaaagctggg gtttcgggaa agttgtattt aagagatatc tcagatacga caggacggaa   240
gcttcactgc acagagtcct tggatcttgg acgggagatt cggttaacta tgcagcatct   300
cgatttctcg gtgccaacca ggtcggatgt acctatagta ttcggtttcg aggagttagt   360
gtcaccattt ctggagggtc gagaactctt cagcatctct gtgagatggc aattcggtct   420
aagcaagaac tgttacagct tacccccagtc gaagtggaaa gtaatgtatc aagaggatgc   480
cctgaaggta ttgaaacctt caagaaagaa agcgagggat ccggaggcgg tgatgaagct   540
gactattcgg cgtaccctga ctcagttcca atgatgtca                          579

<210> SEQ ID NO 7
<211> LENGTH: 36
<212> TYPE: DNA
<213> ORGANISM: Artificial Sequence
<220> FEATURE:
<223> OTHER INFORMATION: Forward primer for p19 protein

<400> SEQUENCE: 7
catatggaac gagctataca aggaaacgac actagg                             36

<210> SEQ ID NO 8
<211> LENGTH: 93
<212> TYPE: DNA
<213> ORGANISM: Artificial Sequence
<220> FEATURE:
<223> OTHER INFORMATION: Reverse primer for p19 protein

```
<400> SEQUENCE: 8
aatatgctcg agtcatgaca tcattggaac tgagtcaggg tacgccgaat agtcagcttc    60
atcaccgcct ccggatccct cgctttcttt ctt                                 93

<210> SEQ ID NO 9
<211> LENGTH: 20
<212> TYPE: DNA
<213> ORGANISM: Artificial Sequence
<220> FEATURE:
<223> OTHER INFORMATION: Forward primer for RFP

<400> SEQUENCE: 9
ggctgcttca tctacaaggt                                                20

<210> SEQ ID NO 10
<211> LENGTH: 20
<212> TYPE: DNA
<213> ORGANISM: Artificial Sequence
<220> FEATURE:
<223> OTHER INFORMATION: Reverse primer for RFP

<400> SEQUENCE: 10
gcgtccacgt agtagtagcc                                                20

<210> SEQ ID NO 11
<211> LENGTH: 20
<212> TYPE: DNA
<213> ORGANISM: Artificial Sequence
<220> FEATURE:
<223> OTHER INFORMATION: Forward primer for beta-actin

<400> SEQUENCE: 11
agagggaaat cgtgcgtgac                                                20

<210> SEQ ID NO 12
<211> LENGTH: 21
<212> TYPE: DNA
<213> ORGANISM: Artificial Sequence
<220> FEATURE:
<223> OTHER INFORMATION: Reverse primer for beta-actin

<400> SEQUENCE: 12
caatagtgat gacctggccg t                                              21
```

RECOMBINANT PROTEIN FOR SIRNA DELIVERY AND COMPOSITION COMPRISING THE SAME

CROSS REFERENCE TO RELATED APPLICATION

This application claims the benefit of Korean Patent Application No. 10-2012-0087882, filed on Aug. 10, 2012, the contents of which is incorporated herein by reference.

FIELD OF THE INVENTION

This invention relates to a recombinant protein for siRNA delivery and a composition comprising the same. More particularly, siRNAs with a variety of purposes can secure their stability from external attacks such as various degradation enzymes by being assembled to the recombinant protein for siRNA delivery, which can have selective binding affinity to cancer cells by virtue of a target-oriented peptide having various cancer cells as its target, and silence a target gene by effectively delivering the siRNAs to cells and biological tissues by the release of the siRNAs to the cytoplasms after the cell penetration thereof.

BACKGROUND OF THE INVENTION

RNA interference (RNAi) refers to a phenomenon where a double stranded RNA consisting of a sense RNA having a homologous sequence with the mRNA of a target gene and an antisense RNA having a complementary sequence therewith is introduced to cells to selectively induce the degradation of the target gene mRNA or suppress the expression of the target gene. The RNAi was first found in nematodes and for now, it is observed in various organisms including yeasts, insects, plants, humans, as a highly preserved biological phenomenon.

A small interference RNA (siRNA), as a material of inducing RNAi, refers to a short double helical strand consisting of about 20 to 30 nucleotides. The introduction of an siRNA into cells enables to target mRNA of which the base sequence is complementary to the siRNA, thereby suppressing the expression of its gene. Hence, the siRNA has been paid much attention as an efficient means capable of controlling a life process to be a target by virtue of its therapeutic effects against diseases, and easy preparation and high target selectivity thereof.

Currently, cancers, virus infection diseases, autoimmune diseases, and neurodegenerative diseases have been studied as diseases to be curable by use of siRNAs, and their potentials as therapeutic agents for age-related macular degeneration (Bevasiranib; Opko Health, Inc., Miami, Fla., USA; clinical phase III) and respiratory syncytial virus infection (ALN-RSV01; Alnylam, Cambridge, Mass., USA; clinical phase II) have been reported as clinical trials thereof. Furthermore, it was reported that the delivery system of siRNAs in human cancer therapy is possible by using cyclodextrine-based nano particle polymers having transferrin as their target (Oh Y K. et al., Adv Drug Deliver Rev 2009, 61, 850-862).

However, the siRNAs are in vivo degraded within a short time due to their low stability and the anionic nature thereof hinders them from readily penetrating cell membranes with the same negative charge, leading to low transmissibility into cells and thus, there is a demand on efficient delivery vehicle technology capable of making their intracellular delivery easy. Accordingly, in order to efficiently deliver siRNAs into cells, there is needed an effective novel delivery system capable of having resistance against degradation enzymes, circulating in living body for a long time and reaching target cells via a clinically available injection route, and enabling an effective cytoplasm release after the cell penetration thereof.

As existing siRNA delivery vehicles, recombinant plasmids or virus vectors of expressing siRNA were used, or lipofectin, lipofectamine, cellfectin, cationic phospholipid nanoparticle, cationic polymer, or liposome-based delivery vehicles were usually used. However, viral delivery vehicles are restricted by the size of a gene to be delivered and they do not guarantee in vivo stability thereof because they might cause immune side effects due to the immunogenicity of the surface proteins of the virus vectors. Further, the delivery vehicles using cationic molecules or synthetic polymers have showed low transport efficiency into cells and had cell toxicity problems which might result from gene delivery procedures into cells.

SUMMARY OF THE INVENTION

Therefore, it is an object of the present invention to provide a recombinant protein for siRNA delivery comprising an siRNA binding protein and a target-oriented peptide.

It is another object of the invention to provide a composition for siRNA delivery comprising the recombinant protein for siRNA delivery and an siRNA.

It is still another object of the invention to provide a composition for treatment of siRNA-associated diseases comprising the recombinant protein for siRNA delivery and an siRNA.

However, the technical goals that the present invention intends to achieve are not limited to those mentioned in the above, and others not mentioned above will be clearly understood from the following descriptions by a skilled person in the pertinent art.

As a means of achieving the aforementioned objects, the present invention provides a recombinant protein for siRNA delivery comprising an siRNA binding protein and a target-oriented peptide, wherein the target-oriented peptide is located on the surface of the siRNA binding protein.

The siRNA binding protein is a protein present in Carnation Italian ringspot virus (CIRV), and it may be a protein which is assembled, with high affinity, with a double stranded RNA of 20 to 23 nucleotides long, preferably may be p19 RNA binding protein (GenBank Accession Number CAA59481.1), more preferably may be a protein containing the amino acid sequence of SEQ ID. No. 1, and most preferably may be p19 RNA binding protein having the amino acid sequence of SEQ ID. No. 1, but not limited thereto, and include all modified forms capable of forming an assembly along with siRNA, where some of SEQ ID. No. 1 is substituted, added, or deleted.

The p19 RNA binding protein according to one embodiment of the present invention, as a protein present in a plant, i.e., Carnation Italian ringspot virus (CIRV), can be assembled with a double stranded RNA of 20 to 23 nucleotides long with high affinity, but it shows peculiarity in that it is not assembled with any of single stranded RNAs, double stranded DNAs and ribosome RNAs and accordingly, it is suitable for the siRNA binding protein of the invention. The p19 RNA binding protein forms an assembled body with siRNA by becoming a homodimer.

In accordance with the present invention, the p19 RNA binding protein may improve transmissibility into target cells by the introduction of a variety of target-oriented peptides using gene recombinant methods and at the same time, it may increase in vivo stability of an siRNA by coupling it at a binding site where the homodimer of the p19 RNA binding proteins is formed and thus protecting the siRNA from external attacks and accordingly, it can be utilized as an effective siRNA delivery vehicle.

The target-oriented peptide of the present invention refers to a peptide of leading delivery to target cells by the introduction thereof to the surface of the recombinant protein for siRNA delivery. The target-oriented peptide may be a peptide binding to EphA2 membrane protein which is overexpressed particularly in cancer cells and having HeyA8, A549, MDA-MB231, SKOV3ip1, B16E10 or HeLa cells as its target cells, preferably may be a peptide containing the amino acid sequence of SEQ ID NO: 3, and more particularly may be YSA peptide (Tyr-Ser-Ala-Tyr-Pro-Asp-Ser-Val-Pro-Met-Met-Ser, SEQ ID NO: 3)

As the YSA peptide is exposed outside the recombinant protein for siRNA delivery and binds to the EphA2 membrane protein which is overexpressed particularly in cancer cells, it may exhibit a targeting property specific to cancer cell.

In accordance with one embodiment of the invention, there may be further included a linker peptide between the siRNA binding protein and the target-oriented peptide.

The linker peptide of the invention, as a peptide linking the p19 RNA binding protein and the YSA peptide, may be those that do not prevent the p19 RNA binding proteins from forming a homodimer therefrom, enable the recombinant protein for siRNA delivery to have siRNA binding ability, and render the YSA peptide to be freely exposed to the surface. Preferably, the linker peptide may be a peptide (GSGGGDEAD) represented by SEQ ID NO: 2 consisting of 9 amino acids.

In accordance with one embodiment of the invention, there may be a recombinant protein for siRNA delivery comprising the following structure:

A-B-C wherein, A is an siRNA binding protein;

B is a linker peptide; and

C is a target-oriented peptide.

In accordance with another embodiment of the invention, there may be a recombinant protein for siRNA delivery comprising the following structure:

A-B-C wherein, A is p19 RNA binding protein;

B is a linker peptide; and

C is a target-oriented peptide containing YSA (SEQ ID NO. 3: Tyr-Ser-Ala-Tyr-Pro-Asp-Ser-Val-Pro-Met-Met-Ser) peptide.

In accordance with another embodiment of the invention, there may be a recombinant protein for siRNA delivery comprising the following structure:

A-B-C wherein, A is p19 RNA binding protein containing the amino acid sequence of SEQ ID NO: 1;

B is a linker peptide containing the amino acid sequence of SEQ ID NO: 2; and

C is a target-oriented peptide containing the amino acid sequence of SEQ ID NO: 3.

As a particular embodiment of the invention, the recombinant protein for siRNA delivery has been designed by sequentially linking the linker peptide and the YSA peptide at $173^{rd}$ amino acid site of the p19 RNA binding protein and actually, the thus designed recombinant protein for siRNA delivery was produced using *E.coli* mass expression system (see Example 1).

Through the quantitative analysis of the above produced recombinant proteins for siRNA delivery, it was confirmed that one siRNA duplex could be enclosed in two recombinant proteins for siRNA delivery (see Example 1).

Further, the recombinant proteins for siRNA delivery were confirmed to have excellent biocompatibility up to 2 μM from their MTT analysis results (see Example 3), and since siRNAs are disassembled from the recombinant proteins for siRNA delivery under acidic conditions, it was confirmed that the siRNAs could be effectively delivered to cytoplasms via endosomal escape mechanism (see Example 4). Since the siRNAs may maintain their stability from external attacks by various ribonucleases by being assembled in the inside of the binding site formed by the recombinant proteins for siRNA delivery (see Example 5), exhibit cancer cell specific cell penetrability by virtue of the target-oriented YSA peptides introduced to the surface of the recombinant proteins for siRNA delivery (see Example 6), and cause the silencing of target genes after the delivery thereof to cytoplasms (see Example 7), they may be effectively employed as an siRNA delivery vehicle.

The present invention provides a composition for siRNA delivery comprising the recombinant protein for siRNA delivery and an siRNA, wherein the siRNA is located inside the recombinant protein. Preferably, the siRNA may include 20 to 30 nucleotides, more preferably may contain a sense sequence of SEQ ID NO: 4 and an antisense sequence of SEQ ID NO: 5, and most preferably may be the sense sequence of SEQ ID NO: 4 and the antisense sequence of SEQ ID NO: 5.

Since the siRNA is assembled to the siRNA binding protein constituting the recombinant protein for siRNA delivery of the present invention, it is characterized by being protected in the inside of the recombinant protein for siRNA delivery. The siRNA assembled in the inside of the recombinant protein for siRNA delivery is physically shielded from the outside, it can show excellent stability, being free from degradation enzymes such as nucleases and it can penetrate into cells by endocytosis after effectively binding to the target cells by virtue of the target-oriented peptide exposed to outside the recombinant protein for siRNA delivery. After the penetration into the cells, the siRNA assembled to the siRNA binding protein is disassembled from the siRNA binding protein under acidic conditions of intracellular endosomes and released into cytoplasms by endosomal escape, it thus can effectively suppress the expression of mRNA. Therefore, it becomes possible to suppress the expression of target genes including disease genes and to treat the diseases.

The present invention provides a composition for treatment of siRNA-associated diseases selected from the group consisting of cancers, age-related macular degeneration, virus infection diseases, autoimmune diseases, and neurodegenerative diseases, comprising the recombinant protein for siRNA delivery and an siRNA, wherein the siRNA is located inside the recombinant protein.

Any siRNAs that can induce disease therapeutic effects by suppressing the expression of diseases-associated genes may be used without any restrictions and preferably, they may include 20 to 30 nucleotides.

The siRNA-associated diseases may include, but not limited to, any diseases known to be curable by siRNAs and preferably they may include diseases selected from the group consisting of cancers, age-related macular degeneration, virus infection diseases, autoimmune diseases, and neurodegenerative diseases. The cancers may include breast cancer, lung cancer, head and neck cancer, brain cancer, abdominal cancer, colon cancer, esophagus cancer, stomach cancer, gastric cancer, liver cancer, tongue cancer, neuroblastoma, osteosarcoma, ovarian cancer, pancreatic cancer, prostate cancer, Phillips' tumor, retinoblastoma, multiple myeloma, skin cancer, lymphoma and blood cancer, but not limited thereto.

The compositions for treatment may be administered to mammals including humans via various routes and they may be administered orally or parenterally (for example, intravenous, subcutaneous, intraperitoneal or local application) according to the methods to be intended, and their dosage may vary by conditions and weight of patients, degree of diseases, type of a drug, route of administration and time, but may be suitably determined by those skilled in the pertinent art.

When the compositions for treatment according to the present invention are to be formulated, they are prepared using diluents or excipients including a filler, an extender, a binder, a wetting agent, a disintegrating agent, and a surfactant which are normally used.

Solid formulations for oral administration may include a tablet, a pill, powders, granules, a capsule, trokije, etc. and such solid formulations are formulated by blending at least one compound according to the present invention with at least one or more excipients, for example, starch, calcium carbonate, sucrose or lactose or gelatin. Furthermore, in addition to the simple excipients, lubricating agents such as magnesium stearate and talc are used. Liquid formulation for oral administration may include a suspension, an oral solution, an emulsion or a syrup, and in addition to water and liquid paraffin which are simple diluents ordinarily used, several excipients, for example, a wetting agent, sweetening agent, flavoring agent, preservative, etc. may be included.

Formulations for parenteral administration may include a sterilized aqueous solution, hydrophobic solvent, suspension, emulsion, lyophilized formulation, suppository, etc.

For the hydrophobic solvent or suspension, there may be used a vegetable oil such as propylene glycol, polyethylene glycol, and olive oil, an injectable ester such as ethyl oleate, etc. For the suppository base, there may be used witepsol, macrogol, tween 61, cacao butter, laurin butter, glycerol, and gelatin.

The compositions for treatment according to the present invention are administered in a pharmaceutically effective amount. The "pharmaceutically effective amount" as used in the present invention refers to a sufficient amount to treat a disease at a reasonable benefit/risk ratio applicable for medical treatment, and an effective dose level can be determined by factors including the type of patient's disease, severity, activity of a drug, sensitivity to a drug, administration time, administration route and excretion ratio, duration of treatment and other drugs to be concurrently used, and other factors well known in the medical field. The compositions for treatment of the invention may be administered as an individual therapeutic agent or in combination with other therapeutic agents, may be administered sequentially or concurrently with existing therapeutic agents, or may be administered in a singular or multiple doses. It is essential to administer in an amount capable of obtaining maximum effects with a minimum amount without incurring any side-effects in light of all the above listed factors, and it can be easily determined by those skilled in the pertinent art.

In particular, the effective amount of the compounds in accordance with the present invention may vary by the age, gender and weight of patients and in general, 0.1 to 100 mg, preferably 0.5 to 10 mg per kg of body weight may be administered daily or on every other day, ranging from one to three times per day. However, since this may be increased or decreased in light of the route of administration, the severity of obesity, gender, weight, age, etc., it should be understood that the dosage suggested above does not limit the scope of the invention in any way.

The recombinant proteins for siRNA delivery of the present invention can secure the stability of siRNAs from external attacks such as various degradation enzymes, have selective binding affinity to cancer cells by virtue of target-oriented peptides having various cancer cells as their targets, and silence target genes by effectively delivering the siRNAs to cells and biological tissues by the release of the siRNAs to the cytoplasms after the cell penetration thereof.

Therefore, the recombinant proteins for siRNA delivery of the invention are expected to be effectively employed as siRNA delivery vehicles for siRNA therapeutic agents, cell-based drug screening compositions and research because they can selectively deliver siRNAs to cancer cells and cancer tissues and innovatively enhance in vivo stability thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows an amino acid sequence containing the recombinant protein for siRNA delivery prepared in Example 1 (showing the amino acid sequence of p19 RNA binding protein (dotted box), a linker peptide of linking p19 RNA binding protein and YSA peptide (solid underline), and YSA peptide (dashed box)).

DETAILED DESCRIPTION OF THE INVENTION

Hereafter, this invention will be described in more detail in light of the following examples. These examples are intended to further illustrate the present invention without limiting the scope of the invention.

EXAMPLES

Example 1

Preparation of Recombinant Protein for siRNA Delivery 1-1. Design of Recombinant Protein for siRNA Delivery The inventors designed a recombinant protein for siRNA delivery and performed a 3-D structure analysis simulation thereof.

First, an amino acid sequence set forth in FIG. 1 which constitutes the recombinant protein for siRNA delivery was determined. As shown in FIG. 1, a total of 172 amino acids constituting p19 RNA binding protein (SEQ ID NO: 1) derived from Carnation Italian ringspot virus (CIRV) was linked to a YSA peptide using 9 amino acids (SEQ ID NO: 2: GSGGGDEAD) as a linker peptide at its C-terminal. The YSA peptide was designed to include 12 amino acids (SEQ ID NO: 3: YSAYPDSVPMMS)

Figure 2:
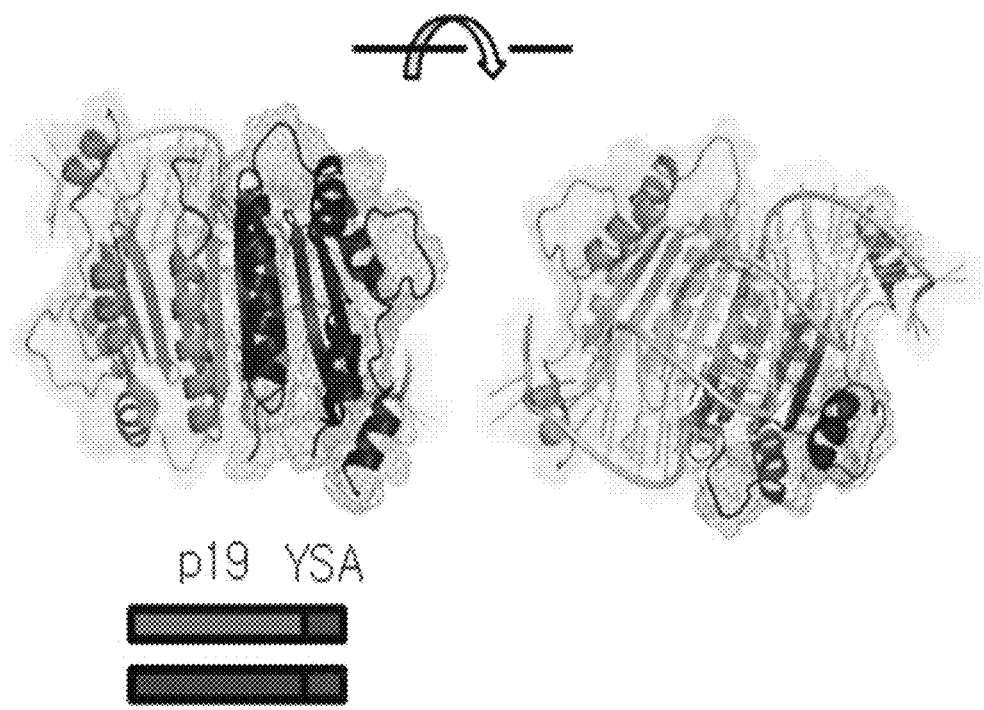
FIG. 2 shows simulation results with regard to the 3-D molecular structure of the recombinant protein for siRNA delivery of the invention.

The thus designed recombinant protein for siRNA delivery (SEQ ID NO: 6) has a 3-D structure as shown in FIG. 2, through structural biology simulation using Pymol (version 1.4.1, DeLano Scientific LLC) 3-D structure analysis program, and the recombinant proteins for siRNA delivery can form a homodimer of two proteins and thus bind to one siRNA duplex.

1-2. Mass Production and Purification of Recombinant Protein for siRNA Delivery Using E.coli In order to produce the recombinant proteins for siRNA delivery designed in Example 1-1 above, a gene encoding the p19 RNA binding protein was amplified by PCR using a forward primer and a reverse primer thereof.

(SEQ ID NO: 7)
5'-CATATGGAACGAGCTATACAAGGAAACGACACTAGG -3'

(SEQ ID NO: 8)
5'-AATATGCTCGAGTCATGACATCATTGGAACTGAGTCAGGGTACGCC

GAATAGTCAGCTTCATCACCGCCTCCGGATCCCTCGCTTTCTTTCTT-

3'

The reverse primer was designed to include genes corresponding to the linker peptide (SEQ ID NO: 2) and the YSA peptide (SEQ ID NO: 3) using gene recombination so that the PCR-amplified product could generate the amino acid sequence corresponding to FIG. 1. The PCR amplification was performed for 30 cycles under conditions of denaturation step at 95° C./30 sec, annealing step at 60° C./30 sec., and elongation step at 72° C./2 min., respectively, and thus a gene construct where genes corresponding to the p19 binding protein (SEQ ID NO: 1), the linker peptide (SEQ D No. 2) and the YSA peptide (SEQ ID NO: 3) are linked to each other could be obtained.

Since the amplified gene contains restriction enzyme sites for NdeI and XhoI, it was purified after the treatment with the restriction enzymes. Likewise, a pET28a vector (NEB Inc.) was purified after the treatment with the same restriction enzymes, inserted with the above recombinant gene using a T4 DNA ligase and then, it was transformed into competent cells using Hanahan method (Hanahan D et al., 1991). This gene insertion was verified using a colony PCR method (Sheu D S et al., 2000) and then, it was finally verified through DNA sequencing.

Figure 3:
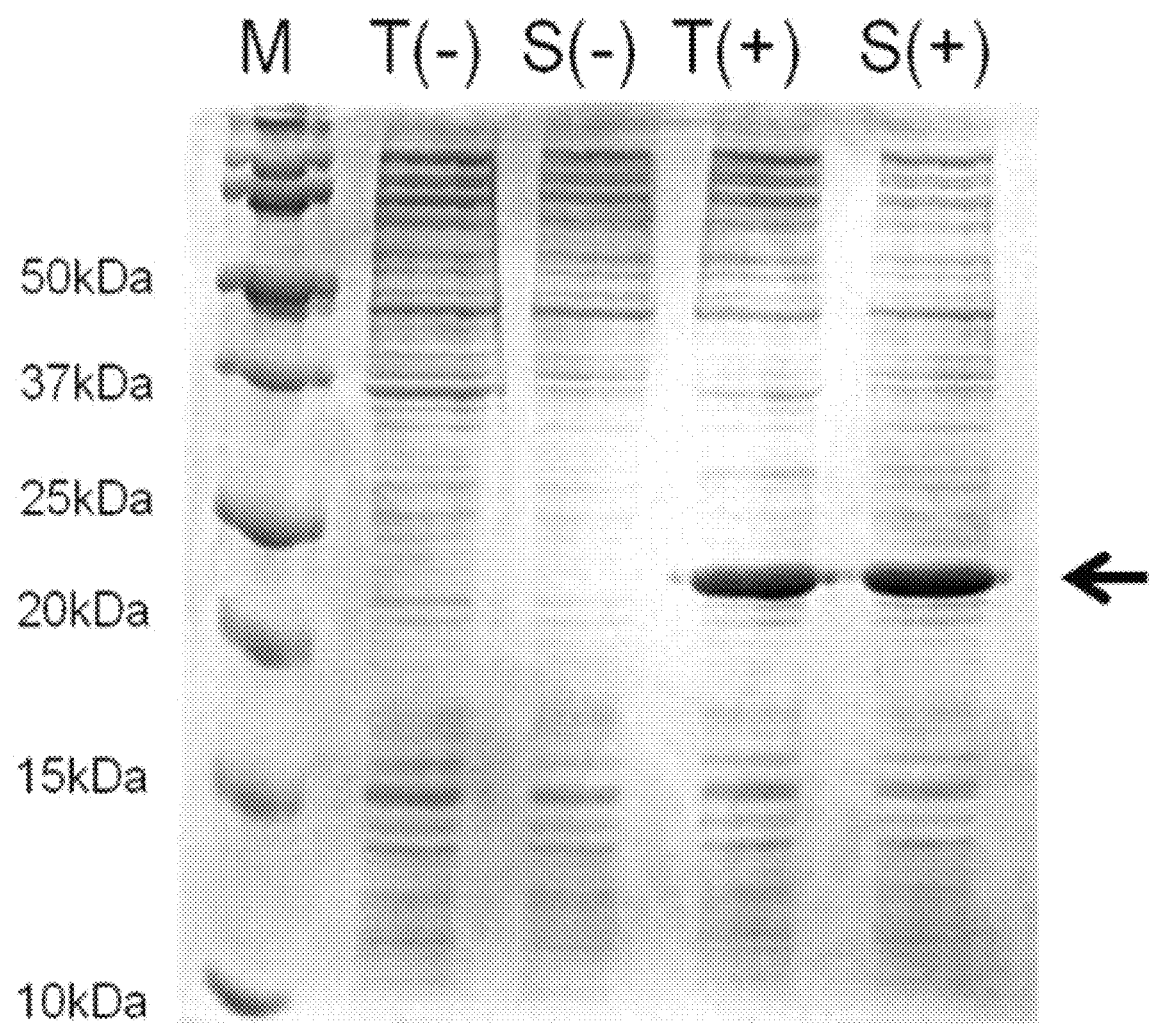
FIG. 3 shows the electrophoresis results obtained when the recombinant protein for siRNA delivery of the invention was induced to be expressed using *E.coli* mass expression system.

After the expression vector inserted with the gene was transformed into BL21(DE3) host cells (Novagen), which were then cultivated in LB media (Sigma-Aldrich) at 37° C. until its $OD_{600}$ value reached 0.5, the expression was induced using 1 mM of IPTG (Isopropyl β-D thiogalactoside) and the results thereof are shown in FIG. 3.

As seen in FIG. 3, the cells of which the protein expression was induced by IPTG exhibited high expression amounts and most of the expressed proteins exhibited excellent solubility.

Thereafter, after further cultivation for 6 hours at 37° C., the cells were harvested and disrupted using a lysis buffer (50 mM Tris-HCl, 8.0, 100 mM NaCl, 1 mM PMSF (phenyl methyl sulfanyl fluoride)) and then, the lysed portion was only used for purification.

Using the presence of a histidine-tag at N-terminal of the recombinant protein for siRNA delivery, which is the characteristic of expression vectors, the purification was carried out using an affinity chromatography.

The affinity chromatography used a Ni-NTA column (GE Healthcare) and after column preparation with A buffer (50 mM Tris-HCl, 8.0, 100 mM NaCl) and protein loading, it was washed. After the proteins attached to the column were eluted with B buffer (50 mM Tris-HCl, 8.0, 100 mM NaCl, 500 mM Immidazole), it was subject to electrophoresis (Laemmli, U. K. Nature 1970, 227, 680-685.) and the results thereof are shown in FIG. 4.

Figure 4:
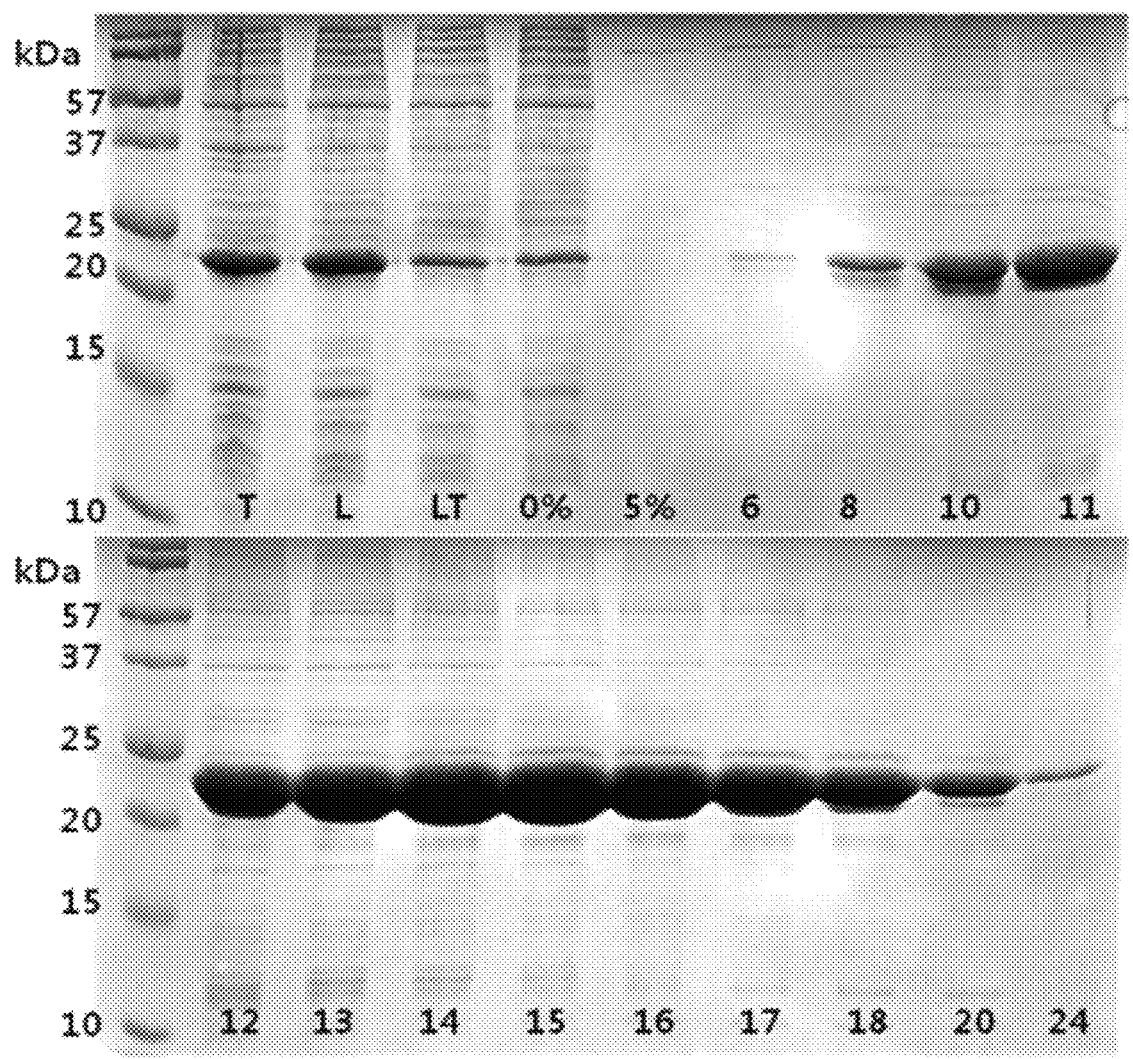
FIG. 4 shows the electrophoresis results obtained when the recombinant protein for siRNA delivery of the invention was purified using histidine affinity column of liquid chromatography.

As seen in FIG. 4, the molecular weight was determined through electrophoresis. After the purification, the concentration of the proteins was concentrated to about 1 mg/Ml and conditions for storage were in 50 mM PBS (7.4).

Example 2 siRNA Binding Strength of Recombinant Protein for siRNA Delivery siRNA strength was examined by enclosing an siRNA into the inside of the recombinant protein for siRNA delivery prepared in Example 1-2 above. In this experiment, the siRNA having an RFP (Red Fluorescent Protein) gene as its target was used and the base sequence of the siRNA used are as follows:

```
                                            (SEQ ID NO: 4)
Sense strand: 5'-UGUAGAUGGACUUGAACUCdTdT-3'

(SEQ ID NO: 5)
Antisense strand: 5'-UGAAGUUGCACUUGAAGUCdTdT-3'
```

Figure 5:
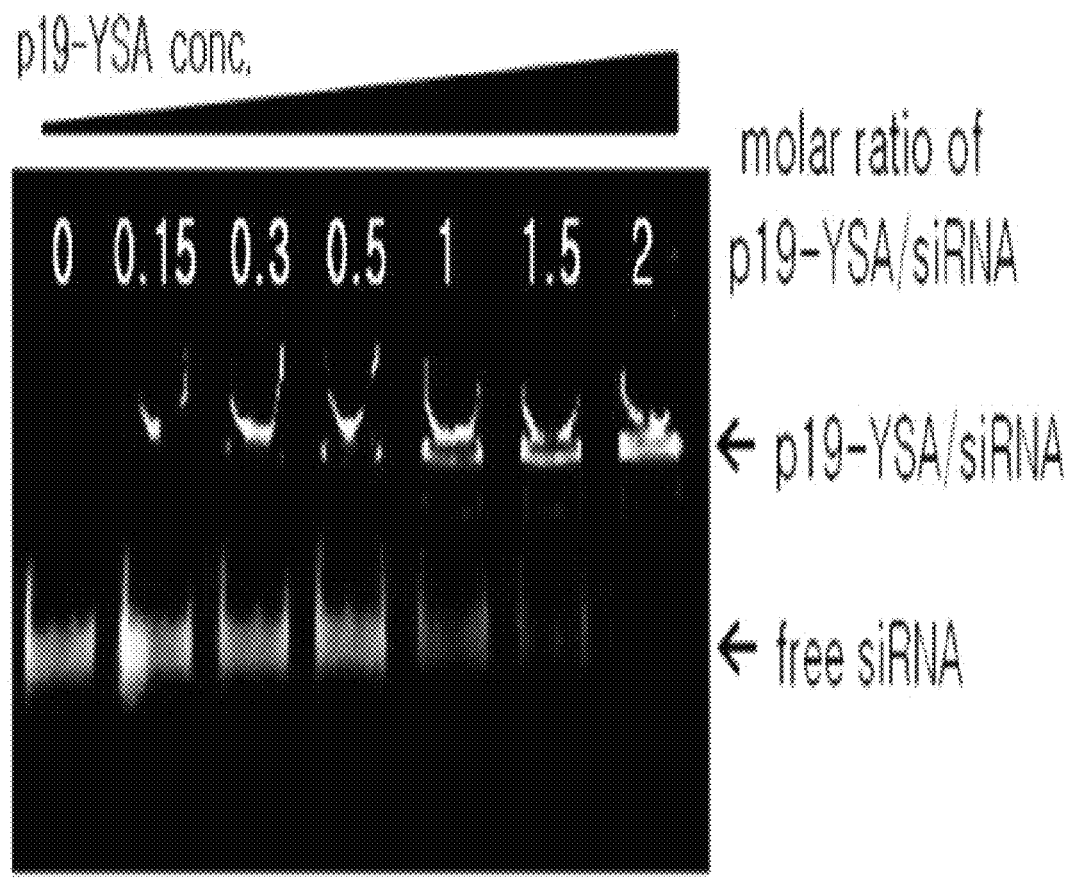
FIG. 5 shows the electrophoresis results obtained from quantitative analysis with regard to the amounts of siRNA to be assembled in proportion to the concentration of the recombinant protein for siRNA in order to investigate an assembly ratio of the recombinant protein of siRNA delivery of the invention and the siRNA (when the amounts of the recombinant protein for siRNA delivery are varied while the amount of siRNA is being fixed, the siRNA participating in the assembly is shown as YSA/siRNA band and the siRNA not participating in the assembly is shown as free siRNA band).

In order to determine a molar ratio of the siRNA to be assembled to the recombinant protein for siRNA delivery, the amount of the siRNA to be assembled was analyzed through electrophoresis as the concentration of the recombinant proteins for siRNA delivery increased in a state of the concentration of free siRNA being fixed, and the results thereof are shown in FIG. 5.

As seen in FIG. 5 as the concentration of the recombinant proteins for siRNA delivery became higher, the thickness of the bands showing a gel shift assembled to the recombinant proteins for siRNA delivery increased because the amount of the siRNAs which do not participate in the assembly decreased, and it was verified through the quantitative analysis thereof that the number of siRNA to be assembled to two recombinant proteins for siRNA delivery is one.

Example 3

Cell Toxicity of Recombinant Protein for siRNA Delivery

In order to examine the intracellular biocompatibility of the recombinant protein for siRNA delivery, MTT analysis was carried out (Choi, Y. H.; Liu, F.; Kim, J. S.; Choi, Y. K.; Park, J. S.; Kim, S. W. J. Control. Rel. 1998, 54, 39-48.).

In particular, after Hela cells in exponential growth phase were cultivated in a 96-well plate until 20000 cells per plate became available, each well was treated with the recombinant proteins for siRNA delivery prepared in Example 1-2 above at various concentrations and then cultured for 24 hours. After the reaction for 4 hours by the addition of 200 uL of MTT solution (0.5 mg/Ml) per well, they were reacted for 10 min. by the addition of 200 uL of DMSO and then, measurement was performed using ELISA at a wavelength of 570 nm and the results thereof are shown in FIG. 6.

Figure 6:
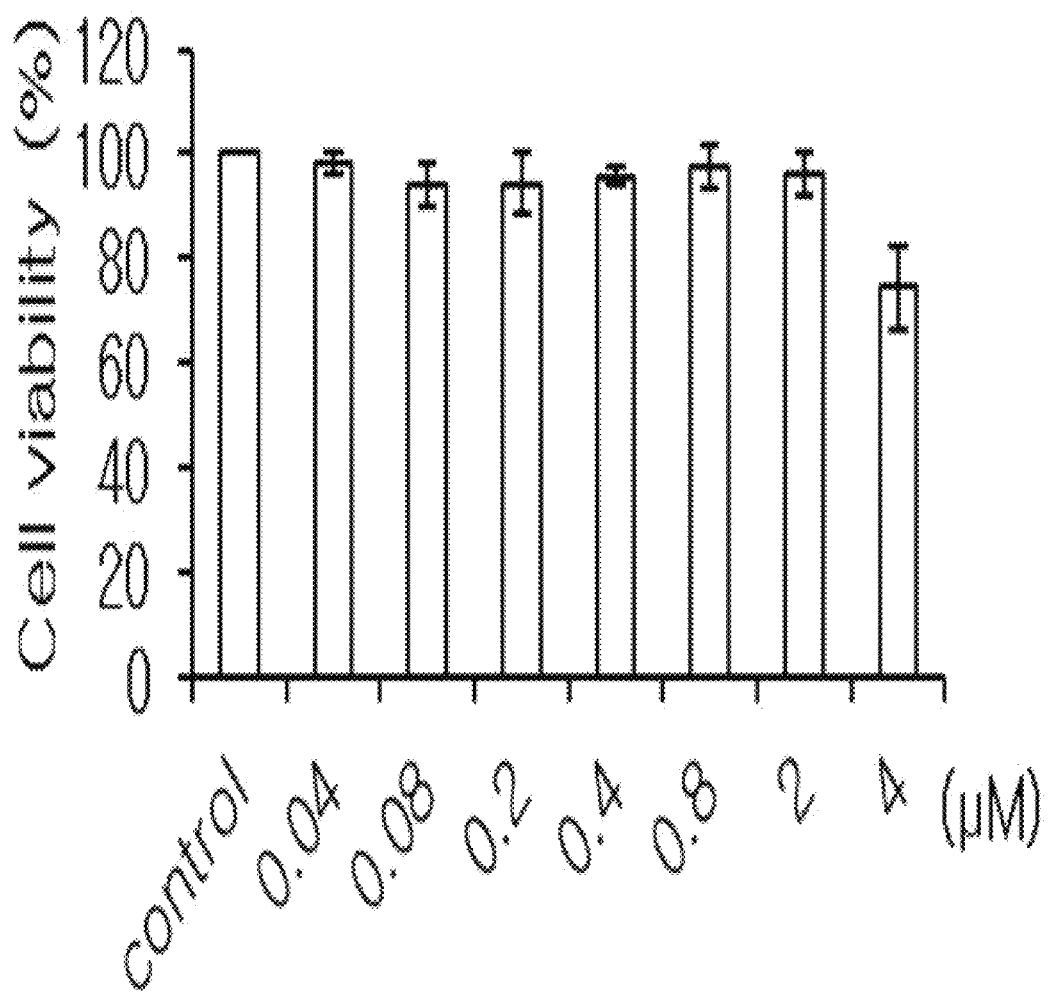
FIG. 6 shows test results for cell toxicity and biocompatibility according to the concentration of the p19-YSA/siRNA assembly of the invention, through MTT analysis.

As seen in FIG. 6, the recombinant proteins for siRNA delivery showed excellent biocompatibility up to 2 μM and preferably, the concentration of the recombinant proteins for siRNA delivery could be determined to be 1 μM.

Example 4 siRNA Binding Strength According to pH of Recombinant Protein for siRNA Delivery An siRNA delivery vehicle is very advantageous when endosomal escape is utilized using the acidic conditions of endosomes in order to be released into cytoplasms after its intracellular penetration by endocytosis.

Hence, siRNA binding strength was measured according to the pH of the recombinant proteins for siRNA delivery prepared in Example 1-2 above. A PBS buffer was used for the condition of pH 7.4, 50 mM sodium acetate buffer was used for the conditions of pH 6.0 to 5.0, and the siRNAs and the recombinant proteins for siRNA delivery were let stand for 10 min. at a room temperature under each corresponding pH condition and then analyzed for their binding levels using electrophoresis (200V, 100 mA), and the results thereof are shown in FIG. 7.

For reference, the siRNAs were attached with a fluorescent substance FITC for easy analysis.

Figure 7:
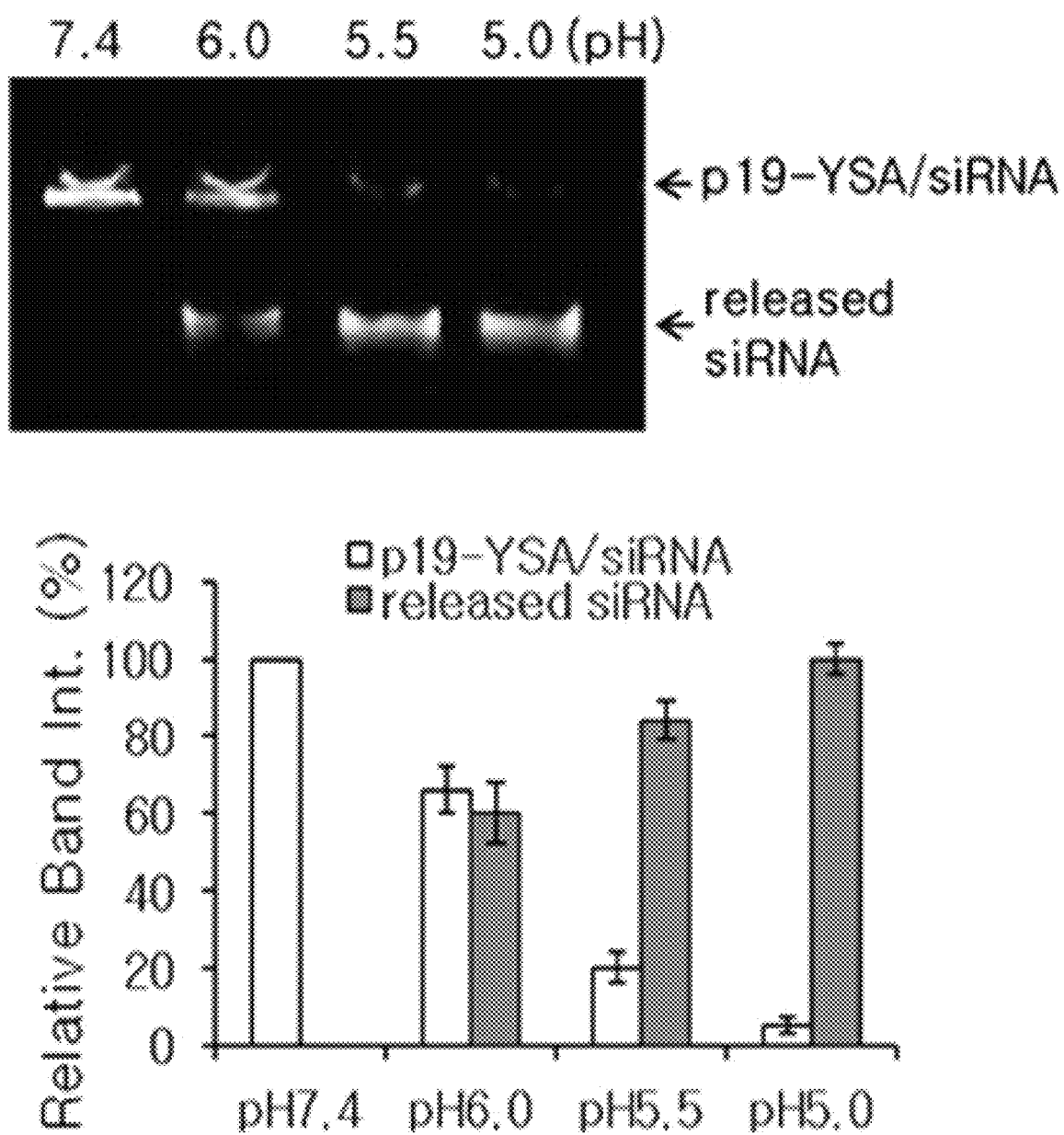
FIG. 7 is electrophoresis results showing that the siRNA being assembled to the p19-YSA/siRNA assembly becomes disassembled as pH decreases.

As seen in FIG. 7, the recombinant proteins for siRNA delivery showed excellent siRNA binding strength at a neutral pH, but they became disassembled as pH decreased. More particularly, the disassembly of the siRNAs was observed, starting from about pH 6.0, and most siRNAs were disassembled at pH of about 5.5.

From such results, it was confirmed that the recombinant proteins for siRNA delivery enable the siRNAs to be delivered into cytoplasms by endosomal escape mechanism after the intracellular penetration thereof.

Example 5

Figure 8:
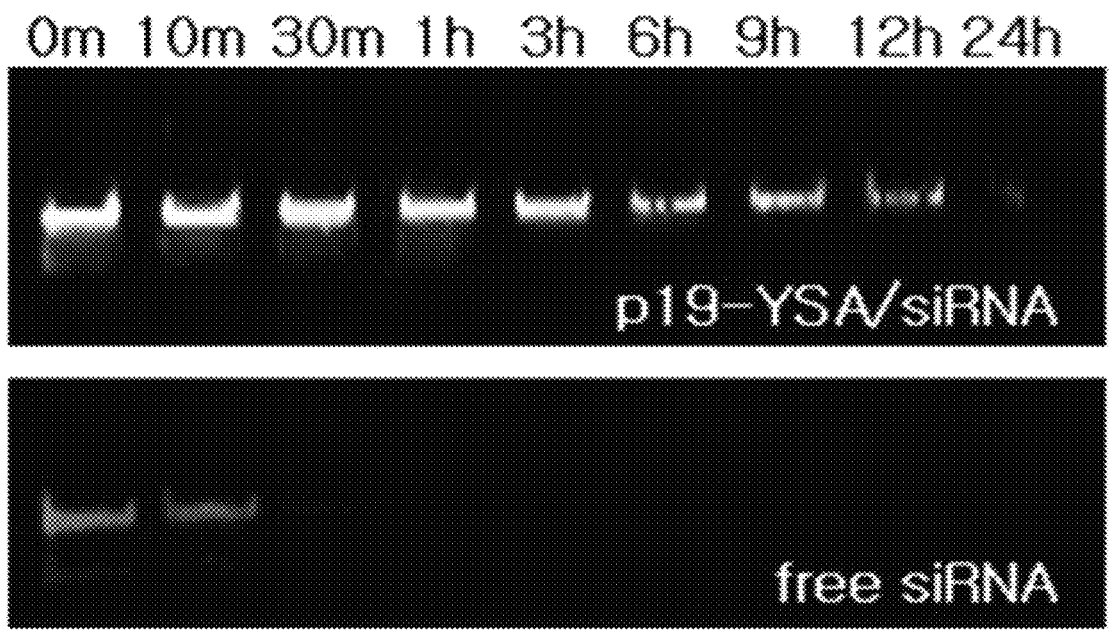
FIG. 8 shows the results contrasting the stability of a naked siRNA and the siRNA being assembled to the recombinant protein for siRNA delivery under 10% FBS (fatal bovine serum) conditions.
Figure 8:
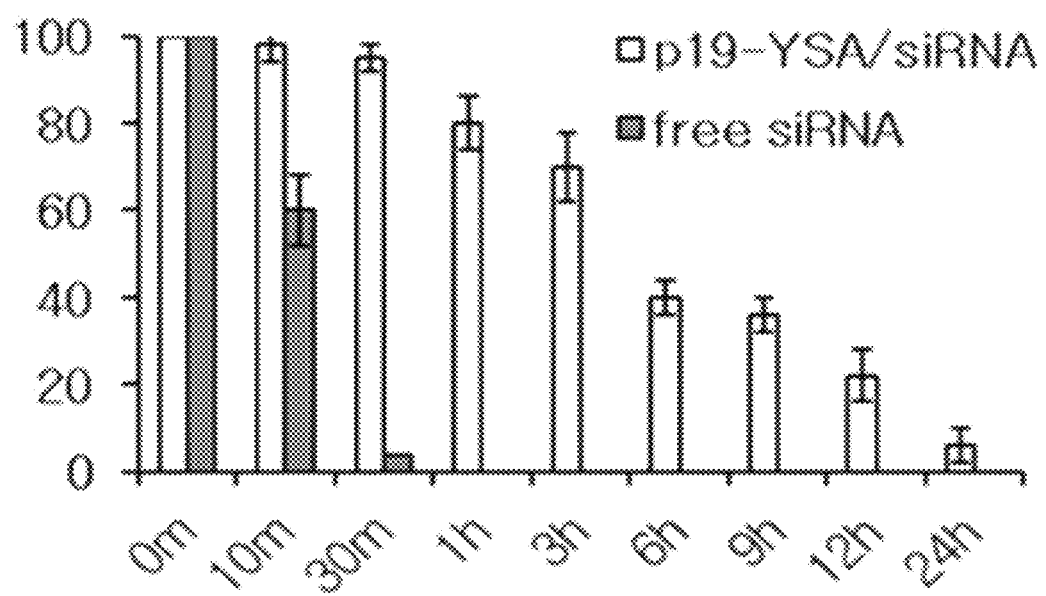

Biological Stability of siRNA Enclosed in Recombinant Protein for siRNA Delivery A naked siRNA and the siRNA enclosed in the recombinant protein for siRNA delivery prepared in Example 1-2 above were let stand under 10% FBS (fatal bovine serum) conditions where various ribonucleases capable of degrading siRNAs coexisted, respectively, according to time at a room temperature and then, levels of being degraded were compared through electrophoresis and the results thereof are shown in FIG. 8.

As seen in FIG. 8, the naked siRNAs were completely degraded within 30 min. whereas the siRNAs protected by being enclosed in the recombinant proteins for siRNA delivery were stable up to about 50% by 6 hours and it was still able to observe remaining siRNAs even in 24 hours.

From such results, it was confirmed that the recombinant protein for siRNA delivery is an excellent delivery vehicle capable of innovatively enhancing the biological stability of siRNAs and further, it was confirmed that the siRNA enclosed in the inside of the recombinant protein for siRNA delivery gets protection physically from external environment by virtue of the p19 RNA binding protein and possesses excellent degradation resistance against ribonucleases.

Example 6

Cell Penetrability of Recombinant Protein for siRNA Delivery

Cell penetration experiments were performed on a mouse myeloma cell line B16F10. Particularly, in order to make fluorescence observation easy using a fluorescence microscope, Cy5.5 fluorescent substance was coupled using a Lysine residue located on the surface of the recombinant protein for siRNA delivery prepared in Example 1-2 above, and siRNA(Cy5.5-p19-YSA/FITC-siRNA assembly) attached with FITC was used. After B16F10 cells were treated with 25 μM of the Cy5.5-p19-YSA/FITC-siRNA assembly, they were observed in an interval of 10 min. using a fluorescence microscope, and the results thereof are shown in FIG. 9.

Axioskop2 FS plus imaging microscope (ZEISS) attached with Achroplan IR40 x/0.80 W lens, Axiocam black and white CCD camera (Carl Zeiss) was used as the fluorescence microscope.

Figure 9:
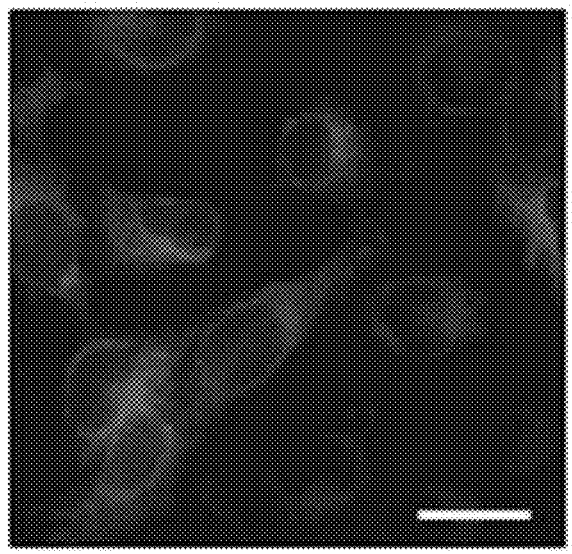
FIG. 9 is fluorescence microscope analysis results showing that the Cy5.5-p19-YSA/FITC-siRNA assemblies which were probed with fluorescent substances Cy5.5 and FITC respectively were penetrated into B16F10 cancer cells (DAPI dye represents the location of cellular nucleus and merge image represents the results overlapped with each image).
Figure 9:
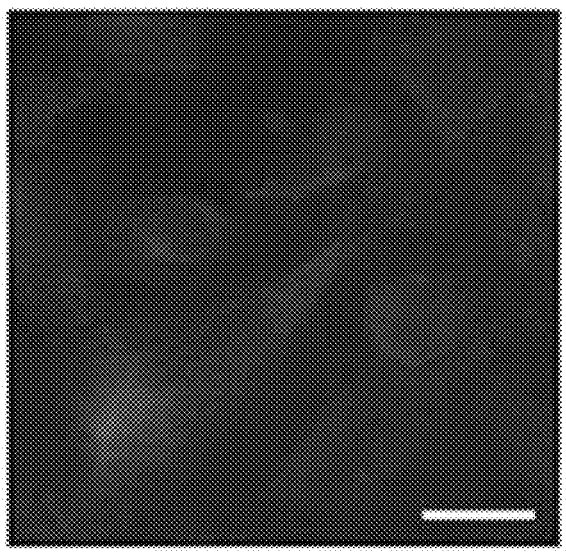
Figure 9:
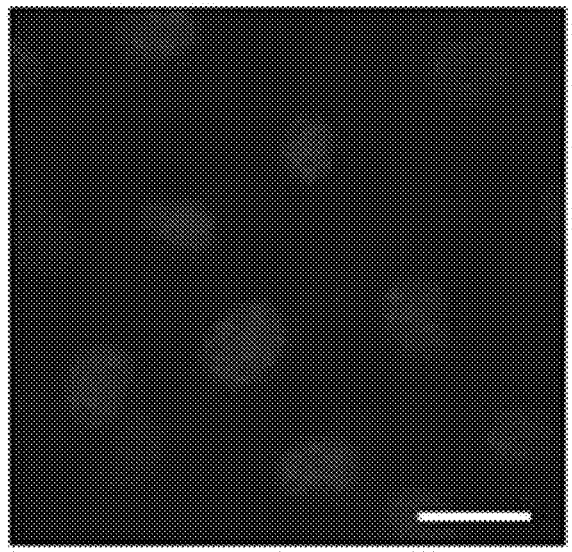
Figure 9:
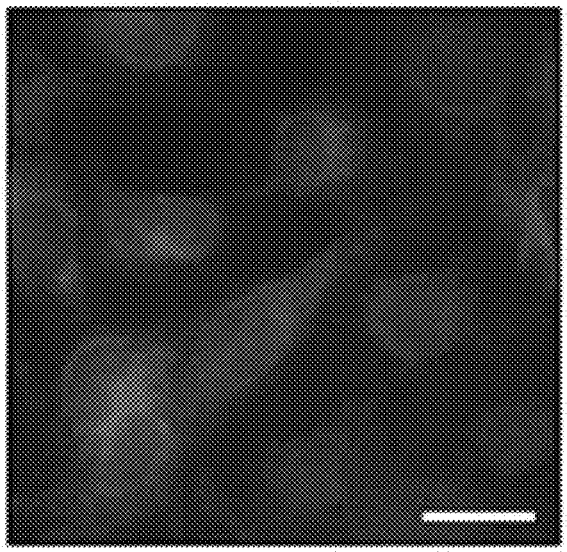

As seen in FIG. 9, the intracellular penetration of p19-YSA and siRNA started to be observed from the lapse of 10 min. after the treatment with the Cy5.5-p19-YSA/FITC-siRNA assembly, and its maximum cell penetration was observed at the lapse of about 30 min. From the results, it was confirmed that the recombinant protein for siRNA delivery has very excellent cell penetrability.

Figure 10:
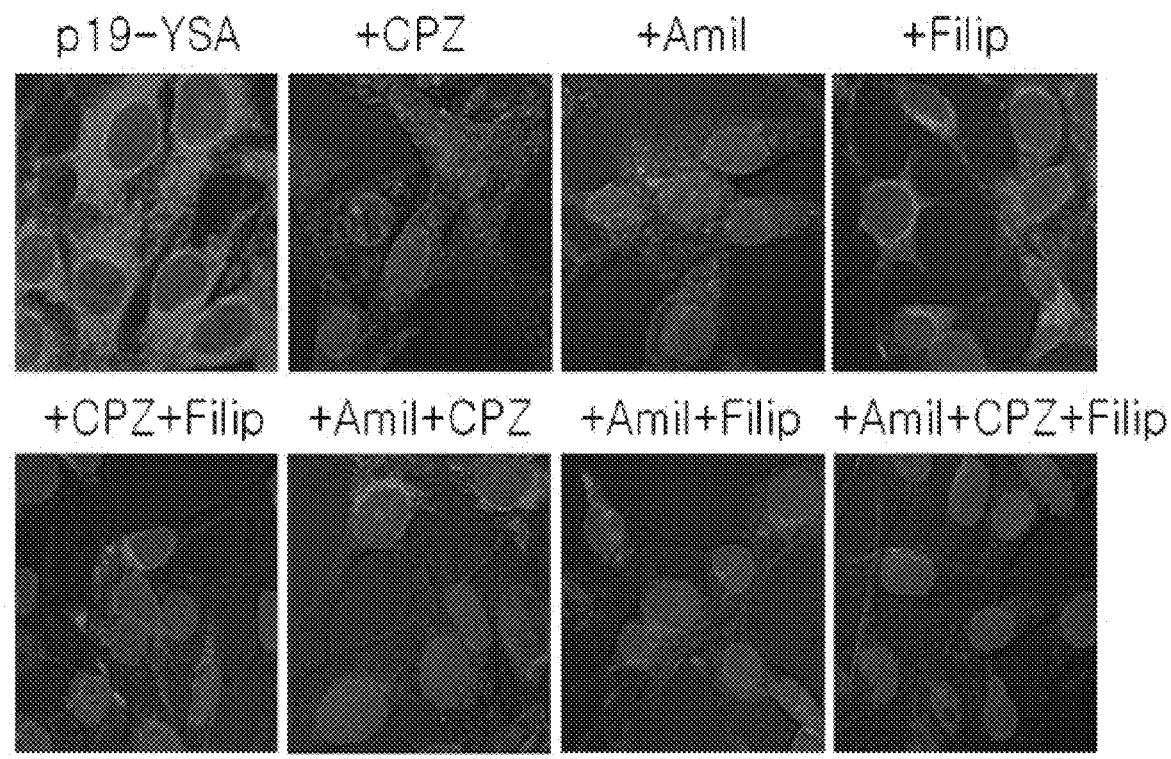
FIG. 10 shows a reduction in cell penetration through fluorescence microscope when one or more inhibitors selected from the group consisting of CPZ, Amil and Filip were treated.
Figure 10:
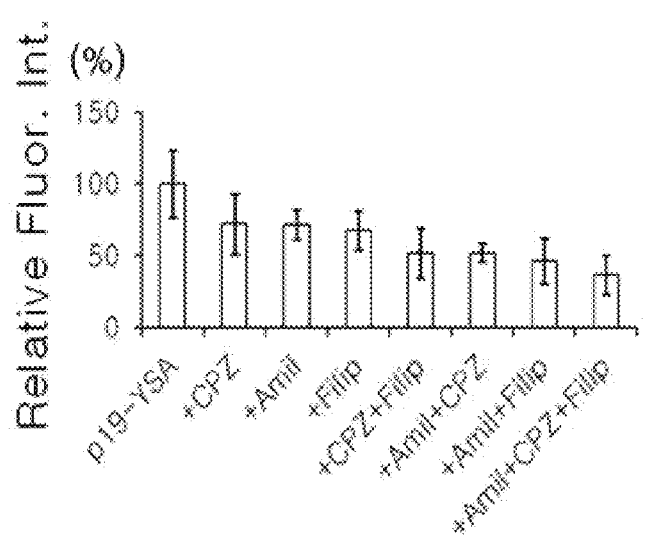

In order to examine cell penetration by endocytosis, the recombinant proteins for siRNA delivery were treated with one or more inhibitors selected from the group consisting of CPZ (Sigma, Ger), Amil (Sigma, Ger) and Filip (Sigma, Ger) which are typical endocytosis inhibitors, and the results thereof are shown in FIG. 10.

As seen in FIG. 10, it was confirmed, through the fact that the cell penetration ability of the recombinant proteins for siRNA delivery was remarkably reduced, that the recombinant proteins for siRNA delivery are penetrated into cells by endocytosis.

After the synthesized YSA peptides (amino acid sequence: SEQ ID NO, 3: YSAYPDSVPMMS) were pre-treated at 100 times higher concentration than the recombinant proteins for siRNA delivery, the Cy5.5-p19-YSA/siRNA assembly was treated, and the results thereof are shown in FIG. 11.

Figure 11:
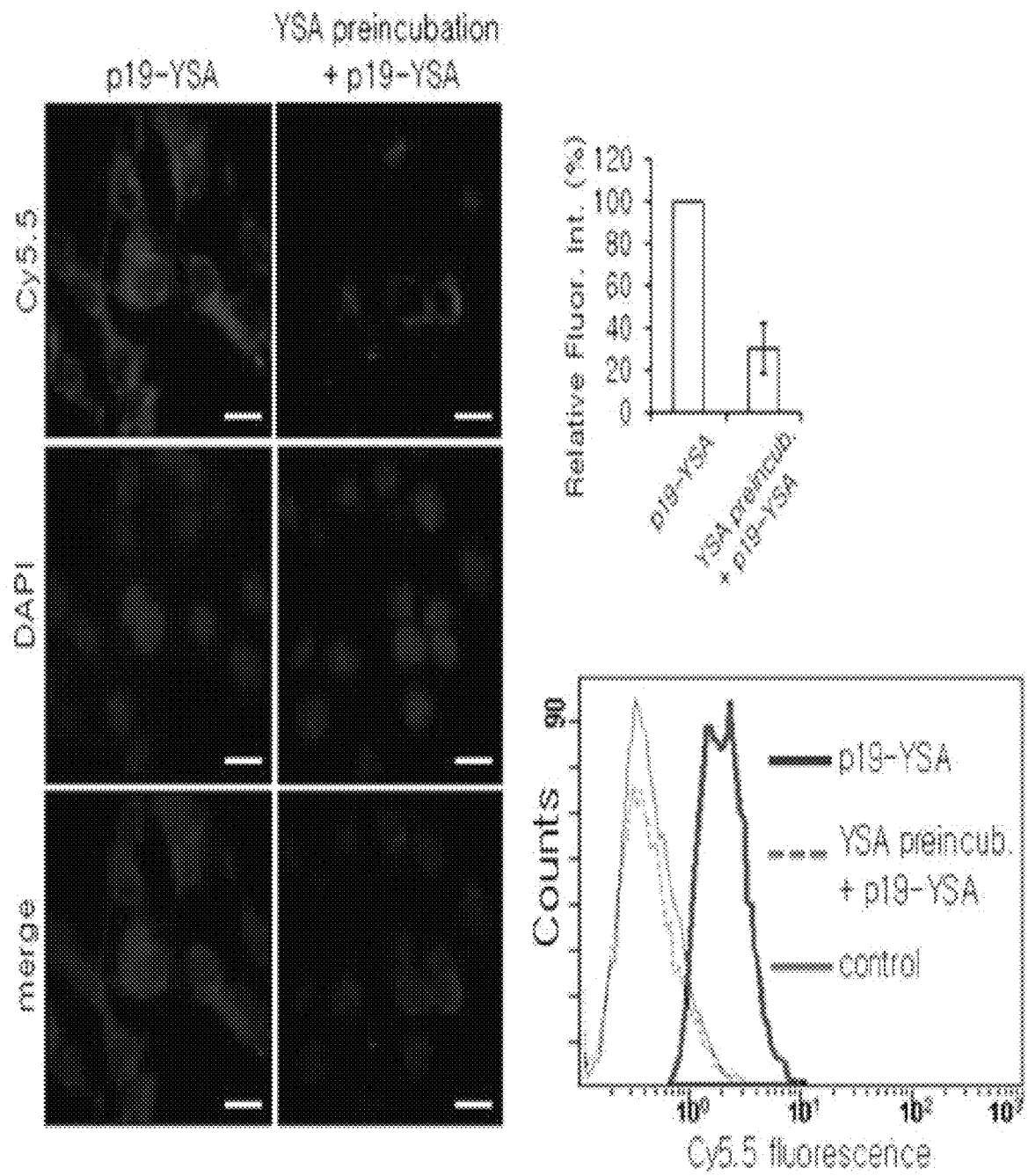
FIG. 11 shows the fluorescence microscope and flow cytometry results obtained after the Cy5.5-p19-YSA/siRNA assembly was treated onto cells which were previously treated with YSA peptides having 100 times high concentrations.

As seen in FIG. 11, the cell penetration ability was observed to be remarkably reduced (70%). The p19-YSA enters inside the cells by interaction between the YSA peptides and EphA2 present on the surface of the cells. However, as the pre-treatment of the synthesized YSA peptides at high concentration renders the EphA2 receptors to be saturated in a state of binding to the YSA peptides, the p19-YSA cannot be interacted with EphA2 any more. Thus, it was confirmed through this result that the recombinant protein for siRNA delivery shows cell penetration ability by virtue of the YSA peptide exposed to the surface thereof. Furthermore, it was confirmed through flow cytometry analysis that when the recombinant proteins for siRNA delivery were treated after the saturation with the YSA peptides, cell penetration ability was remarkably reduced.

In conclusion, it was confirmed that excellent cell penetrability is due to the endocytosis by the YSA peptides exposed to the surface of the recombinant proteins for siRNA delivery.

Figure 12A:
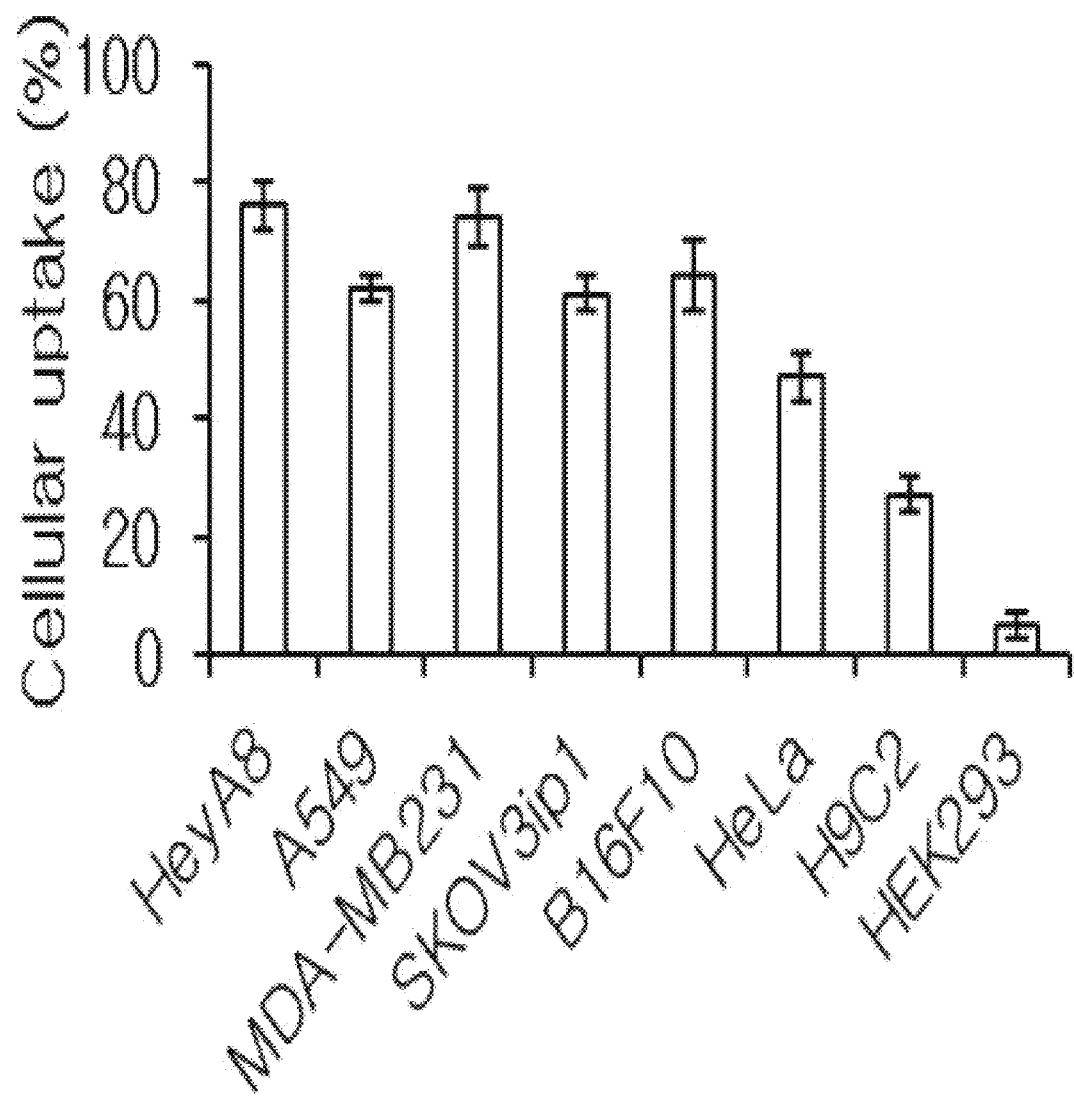
FIG. 12a and FIG. 12b show the flow cytometry results obtained after the Cy5.5-p19-YSA/siRNA assembly was treated onto HeyA8, A549, MDA-MB231, SKOV3ip1, B16F10, HeLa, H9C2 and HEK293 cells.
Figure 12B:
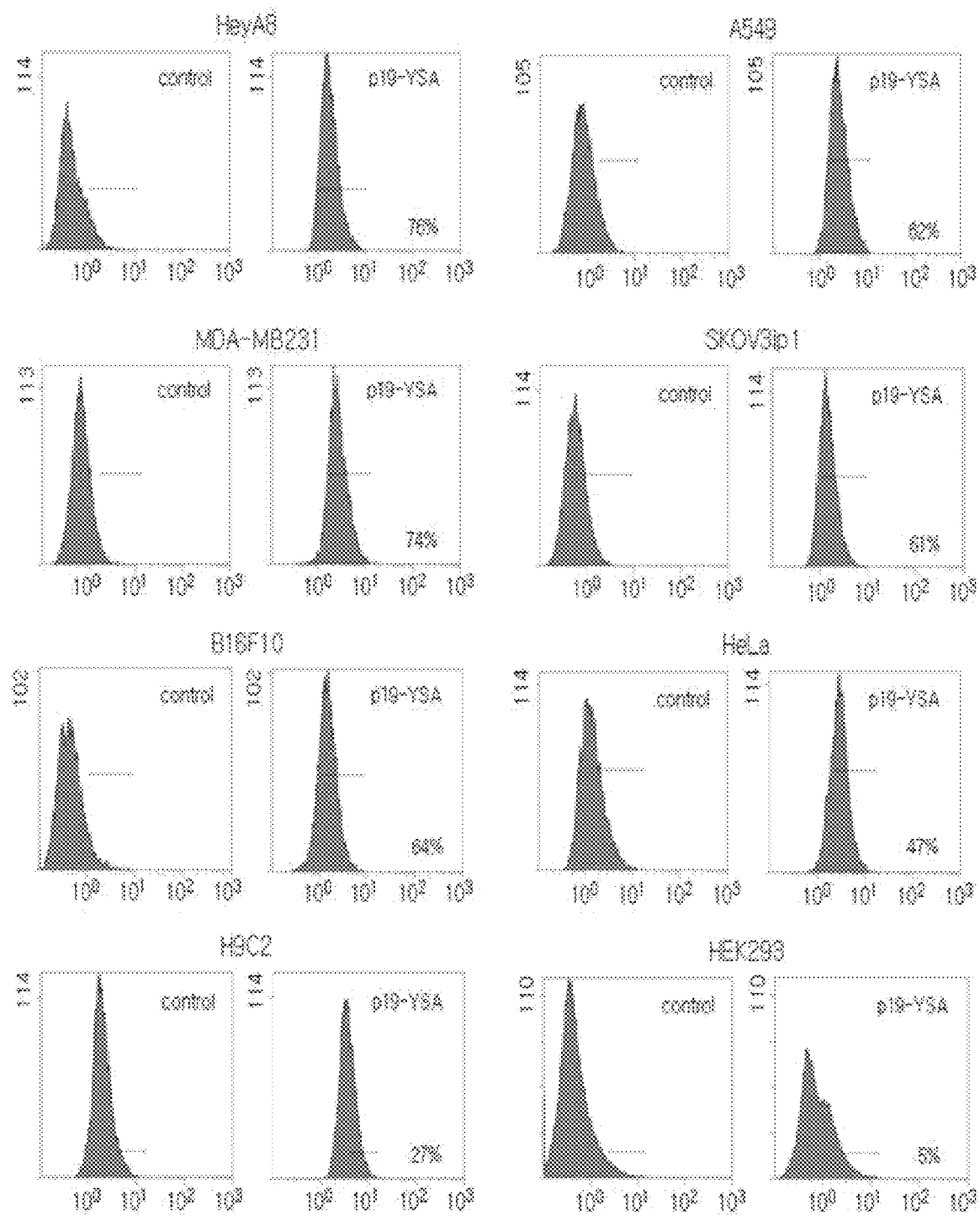

In order to investigate cell binding ability selective to cancer cells using EphA2 membrane proteins specifically over-expressed in cancer cells, HeyA8, A549, MDA-MB231, SKOV3ip1, B16F10, and HeLa cells which are typical cancer cells, and H9C2 and HEK293 which are typical normal cells were treated with the Cy5.5-p19-YSA/siRNA assembly, and flow cytometry analysis was then performed and the results thereof are shown in FIG. 12.

As seen in FIG. 12, it was confirmed that the Cy5.5-p19-YSA/siRNA assembly showed excellent cell penetrability with regard to cancer cells and from this, it was confirmed that the recombinant protein for siRNA delivery has excellent cell penetrability with regard to cancer cells.

Example 7

Intracellular siRNA delivery by Recombinant Protein for siRNA Delivery and Gene Silencing Gene silencing effects with regard to intracellular genes by the siRNA using the recombinant protein for siRNA delivery as a delivery vehicle were compared with an existing siRNA delivery vehicle, lipofectamine (Invitrogen, USA).

Figure 13:
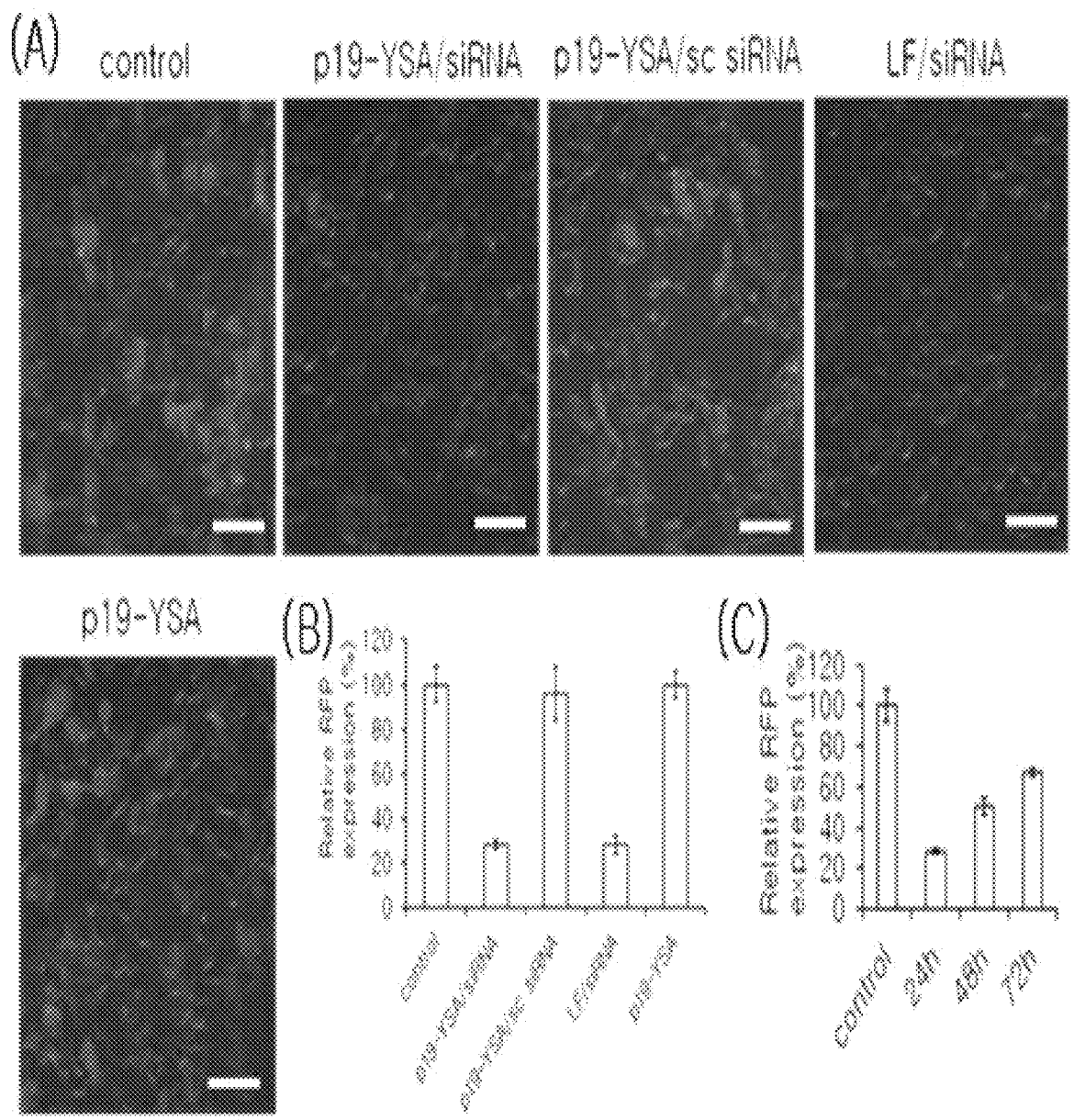
FIG. 13 shows the fluorescence microscope analysis results (picture A) obtained after the p19-YSA/siRNA assembly was treated onto cancer cells (RFP/B16F10) where fluorescent protein RFP is expressed, quantitative analysis results thereof (picture B), and results showing gene expression suppression effects according to time (picture C) (Control: B16F10 cells where RFG genes are expressed, p19-YSA/siRNA: case where siRNA is injected into cells using the recombinant protein for siRNA delivery, p19-YSA/sc siRNAN: case where the recombinant protein for siRNA delivery enclosed with a scramble siRNA which does not match RFP gene is injected into cells, LF/siRNA: case where lipofectamine, which is an existing siRNA delivery vehicle, is only used, and p19-YSA: case where only the recombinant protein for siRNA delivery is injected without siRNA).

The B16F10 myeloma cell line capable of expressing RFP fluorescent proteins was treated with lipofectamine and the recombinant protein for siRNA delivery prepared in Example 1-2 above which were mixed with the same amount of siRNA, respectively and then, after 24 hours, it was observed using a fluorescence microscope and the results thereof are shown in FIG. 13.

As seen in FIG. 13, it was confirmed that the control cells treated with no siRNA showed strong fluorescence intensity by expressing RFP fluorescent proteins, but the siRNA treated with the lipofectamine and the recombinant protein for siRNA delivery suppressed the expression of the REP fluorescent proteins in the cells.

Furthermore, when a scramble siRNA which does not match the RFP protein-coding gene was mixed with the recombinant proteins for siRNA delivery, gene silencing was hardly observed. When the gene silencing of the RFP fluorescent proteins was quantitatively analyzed, the siRNA treated with the lipofectamine suppressed gene expression by about 70% and the siRNA treated with the recombinant protein for siRNA delivery suppressed by about 70%.

Further, the inventors investigated the siRNA delivery effects of the recombinant proteins for siRNA delivery through the analysis of the amount of intracellular RFP mRNA using RT-PCR. More particularly, RT-PCR was performed using primers capable of matching RFP mRNA (forward primer 5'-GGCTGCTTCATCTACAAGGT-3' (SEQ ID NO: 9) and reverse primer 5'-GCGTCCACGTAGTAG-TAGCC-3' (SEQ ID NO: 10)) and primers of matching β-actin for control experiment (forward primer 5'-AGAGG-GAAATCGTGCGTGAC-3' (SEQ ID NO: 11) and reverse primer 5'-CAATAGTGATGACCTGGCCGT-3' (SEQ ID NO: 12) so as to quantify the amount of mRNA of intracellular RFP gene (denaturation step 95° C./30 sec., annealing step 51° C./30 sec., elongation step 72° C./30 sec., 20 cycles), and quantitative analysis with regard to each band after electrophoresis was performed using DNR's GelQuant (image analysis) program and the results thereof are shown in FIG. 14.

Figure 14:
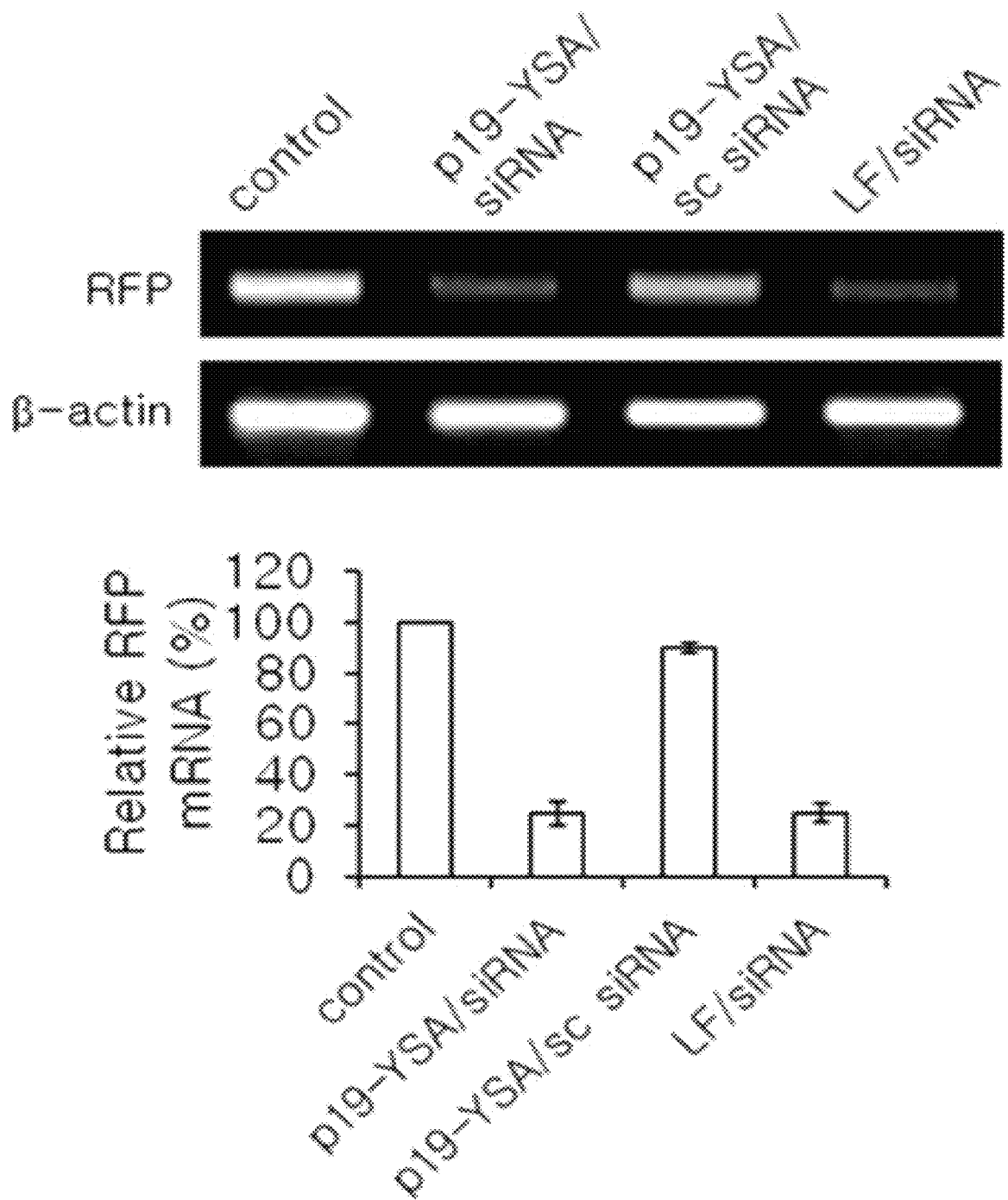
FIG. 14 is electrophoresis results and quantitative analysis results showing that the mRNA of RFP gene in FIG. 13 was degraded by the siRNA, through RT-PCR (Control: B16F10 cells where RFG genes are expressed, p19-YSA/siRNA: case where siRNA is injected into cells using the recombinant protein for siRNA delivery, p19-YSA/sc siRNAN: case where the recombinant protein for siRNA delivery enclosed with a scramble siRNA which does not match RFP gene is injected into cells, LF/siRNA: case where lipofectamine, which is an existing siRNA delivery vehicle, is only used).

As seen in FIG. 14, the siRNA treated along with the lipofectamine showed reduction by about 70% and the siRNA treated along with the recombinant protein for siRNA delivery showed reduction by about 70%, when compared to the control.

Figure 15:
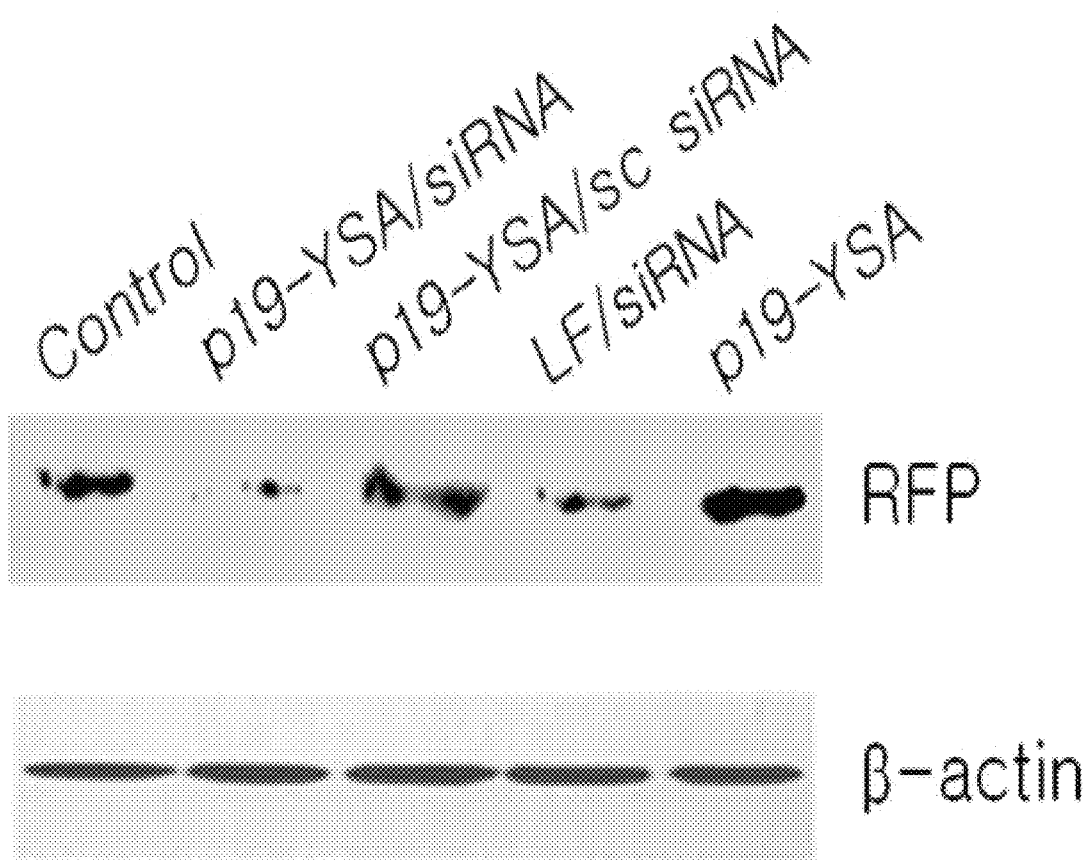
FIG. 15 is western blot results showing that the mRNA of RFP gene in FIG. 13 was degraded by the siRNA and thus the expression of RFP protein was reduced, using RFP antibody (Control: B16F10 cells where RFG genes are expressed, p19-YSA/siRNA: case where siRNA is injected into cells using the recombinant protein for siRNA delivery, p19-YSA/sc siRNAN: case where the recombinant protein for siRNA delivery enclosed with a scramble siRNA which does not match RFP gene is injected into cells, LF/siRNA: case where lipofectamine, which is an existing siRNA delivery vehicle, is only used).

Further, when the suppression of gene expression was investigated using an RFP antibody, as seen in FIG. 15, the detection of the RFP proteins was remarkably reduced in the cells treated with the siRNA using either lipofectamine or the recombinant protein for siRNA delivery, unlike the control cells in which the RFP fluorescent proteins were expressed. When a scramble gene which does not match RFP protein-coding gene was treated with the recombinant protein for siRNA delivery, little gene silencing was observed.

Through this, it was confirmed that the siRNAs delivered into cells by the recombinant proteins for siRNA delivery cause gene silencing.

The foregoing description of the present invention are provided for illustration purpose, and it should be understood that other modified embodiments can be easily made without departing from the spirit and essential features of the invention by a person having ordinary knowledge in the art to which the invention pertains. Therefore, the examples described in the above should be understood to be illustrative and non-restrictive in every aspect.

What is claimed is:

1. A recombinant protein for siRNA delivery, comprising: the siRNA containing a sense sequence of SEQ ID NO: 4 and an antisense sequence of SEQ ID NO: 5, and containing the following structure:

A-B-C wherein, A is a p19 RNA binding protein;

B is a linker peptide; and

C is a target-oriented peptide consisting of amino acid sequence of SEQ ID NO: 3.

2. The recombinant protein of claim 1, wherein the p19 RNA binding protein contains an amino acid sequence of SEQ ID NO: 1.

3. The recombinant protein of claim 1, wherein, A contains an amino acid sequence of SEQ ID NO: 1; and B contains an amino acid sequence of SEQ ID NO: 2.

4. A composition for siRNA delivery comprising the recombinant protein for siRNA delivery according to claim 1 and an siRNA, wherein the siRNA is located inside the recombinant protein.

5. A composition for treatment of siRNA-associated diseases selected from the group cancers, age-related macular degeneration, virus infection diseases, autoimmune diseases, and neurodegenerative diseases, comprising the recombinant protein for siRNA delivery according to claim 1 and an siRNA, wherein the siRNA is located inside the recombinant protein.

6. The composition of claim 4, wherein

A contains an amino acid sequence of SEQ ID NO: 1; and

B contains an amino acid sequence of SEQ ID NO: 2.

7. The composition of claim 5, wherein

A contains an amino acid sequence of SEQ ID NO: 1; and

B contains an amino acid sequence of SEQ ID NO: 2.

* * * * *